US00PP11111P

United States Patent [19]

Oliver

[11] Patent Number: Plant 11,111

[45] Date of Patent: Oct. 26, 1999

[54] HEUCHERA PLANT NAMED 'HARMONIC CONVERGENCE'

[76] Inventor: Charles G. Oliver, R.D. 2, Box 110, Scottdale, Pa. 15683

[21] Appl. No.: 09/005,617

[22] Filed: Jan. 12, 1998

[51] Int. Cl.[6] ..... A01H 5/00

[52] U.S. Cl. ..... Plt./263

[58] Field of Search ..... Plt./263, 68.1

[56] References Cited

U.S. PATENT DOCUMENTS

P.P. 8,984 11/1994 Heims ..... Plt./263

*Primary Examiner*—Howard J. Locker

*Assistant Examiner*—Kent L. Bell

*Attorney, Agent, or Firm*—C. A. Whealy

[57] ABSTRACT

A distinct cultivar of Heuchera plant named 'Harmonic Convergence', characterized by its proportional plants with respect to quantity of flowers to foilage density; unique dark green and silver green-marbled foliage; numerous showy, fringed pink flowers on upper half of cone-like flowering stems; long flowering period with numerous secondary flowering stems; and excellent garden performance.

1 Drawing Sheet

The present invention relates to a new and distinct cultivar of Heuchera, botanically known as *Heuchera sp.*, and hereinafter referred to by the cultivar name 'Harmonic Convergence'. The new cultivar is a product of a planned breeding program conducted by the inventor in Scottdale, Pa. The objective of the breeding program is to create new garden-type Heuchera cultivars having good flower to foliage proportion; numerous large, showy and attractive flowers; attractive foliage; and good garden performance. The new cultivar was selected by the inventor from seedling progeny from a cross made in 1994 by the inventor of the *Heuchera sp.* cultivar 'Quilter's Joy ' (not patented) as the male or pollen parent with the *Heuchera sp.* cultivar 'Regina ' (not patented) as the female or seed parent. The new cultivar was selected by the inventor at his nursery in Scottdale, Pa. from these seedlings. Asexual reproduction of the new cultivar by divisions and by shoot cuttings taken at Scottdale, Pa., has shown that the unique features of this new Heuchera plant are stable and reproduced true to type in successive generations of asexual reproduction. In side-by-side comparisons in Scottdale, Pa., under commercial practice, plants of the new Heuchera are different from plants of the male parent, the cultivar 'Quilter's Joy ' in the following characteristics:

1. Inflorescences of plants of the new Heuchera are more numerous, have more flowers, are denser, and are more uniform in shape than inflorescences of plants of the cultivar 'Quilter's Joy'.

2. Proportion of flowers to foliage is more aesthetically pleasing on plants of the new Heuchera compared to plants of the cultivar 'Quilter's Joy'.

3. Individual flowers of plants of the new Heuchera are larger and more showy than flowers of plants of the cultivar 'Quilter's Joy'.

4. Flowers of plants of the new Heuchera are pink in color compared to plants of 'Quilter's Joy' which have white flowers.

5. Plants of the new Heuchera flower for a longer period of time than plants of the cultivar 'Quilter's Joy'.

In side-by-side comparisons in Scottdale, Pa., under commercial practice, plants of the new Heuchera are different from plants of the female parent, the cultivar 'Regina' in the following characteristics:

1. Leaves of plants of the new Heuchera lack the metallic sheen during the autumn and winter that is present on leaves of plants of the cultivar 'Regina'.

2. Inflorescences of plants of the new Heuchera are more numerous, have more flowers, are denser, and are more uniform in shape than inflorescences of plants of the cultivar 'Regina'.

3. Plants of the new Heuchera are more compact and proportion of flowers to foliage is more aesthetically pleasing on plants of the new Heuchera compared to plants of the cultivar 'Regina'. In addition, flowering stems of plants of the new Heuchera are stronger than flowering stems of plants of the cultivar 'Regina'.

4. Individual flowers of plants of the new Heuchera are larger and more showy than flowers of plants of the cultivar 'Regina'.

5. Plants of the new Heuchera flower for a longer period of time than plants of the cultivar 'Regina'.

The following traits have been repeatedly observed and are determined to be the unique characteristics of 'Harmonic Convergence'. These characteristics in combination distinguish the new heuchera plant as a new and distinct cultivar:

1. Proportional plants with respect to quantity of flowers to foliage density.

2. Unique dark green and silver green-marbled foliage.

3. Numerous showy, fringed pink flowers on upper half of cone-like flowering stems.

4. Long flowering period with numerous secondary flowering stems that develop through the summer.

5. Excellent garden performance.

The new Heuchera plant has not been observed under all possible environmental conditions. The phenotype may vary significantly with variations in environment such as temperature, light level, nutrition and water status without, however, any variance in genotype. Plants of the new Heuchera can be compared to plants of the commercial cultivar 'Pewter Veil' (disclosed in U.S. Plant Pat. No. 8,984). In side-by-side comparisons in Scottdale, Pa., under commercial practice, plants of the new Heuchera are different from plants of the cultivar 'Pewter Veil' in the following characteristics:

1. Inflorescences of plants of the new heuchera are larger, more numerous, are denser with more flowers, and are more uniform in shape than inflorescences of plants of the cultivar 'Pewter Veil'.

2. Plants of the new Heuchera are more compact and proportion of flowers to foliage is more aesthetically pleasing on plants of the new Heuchera compared to plants of the cultivar 'Pewter Veil'.

3. Individual flowers of plants of the new Heuchera are larger and more showy than flowers of plants of the cultivar 'Pewter Veil'.

4. Flowers of plants of the new Heuchera are pink in color compared to plants of 'Pewter Veil' which have yellow-green flowers.

Plants of the new Heuchera can be compared to plants of the nonpatented commercial cultivar 'Montrose Ruby'. In side-by-side comparisons in Scottdale, Pa., under commercial practice, plants of the new Heuchera are different from plants of the cultivar 'Montrose Ruby' in the following characteristics:

1. Inflorecences of plants of the new Heuchera are larger, more numerous, are denser with more flowers, and are more uniform in shape than infloresences of plants of the cultivar 'Montrose Ruby'.

2. Plants of the new Heuchera are more compact and proportion of flowers to foliage is more aesthetically pleasing on plants of the new Heuchera compared to plants of the cultivar 'Montrose Ruby'.

3. Individual flowers of plants of the new Heuchera are larger and more showy than flowers of plants of the cultivar 'Montrose Ruby'.

4. Flowers of plants of the new Heuchera are pink in color compared to plants of 'Montrose Ruby' which have white flowers.

5. Leaves of plants of the new Heuchera have bolder markings with more contrast than leaves of plants of 'Montrose Ruby'.

BRIEF DESCRIPTION OF THE PHOTOGRAPHS

The accompanying colored photographs illustrates the overall appearance of the new cultivar, showing the colors as true as it is reasonably posible to obtain in colored reproductions of this type.

The photograph at the top of the sheet comprises a top perspective view of a one-year plant of 'harmonic Covergence'.

The photograph at the bottom of the sheet comprises a close-up view of a typical flowering stem of 'Harmonic Convergence'. Flower and foilage colors in the photographs may appear different from the actual colors due to light reflectance.

DETAILED BOTANICAL DESCRIPTION

The following observations, measurements, values, and comparisons describe plants grown in Scottdale, Pa., in a glass-covered greenhouse with day temperatures ranging from 16 to 27° C and night temperatures ranging from 4 to 16° C depending upon the season. In the following description, color references are made to The Royal Horticultural Society Colour Chart except where general terms of ordinary dictionary significance are used.

Classification:

*Botanical.*—*Heuchera sp.* cultivar 'Harmonic Convergence'.

Parentage:

*Male or pollen parent.*—*Heuchera sp.* cv. 'Quilter's Joy' (not patented).

*Female or seed parent.*—*Heuchera sp.* cv. 'Regina' (not patented).

Propagation:

*Type.*—By divisions, by shoot cuttings or by tissue culture.

*Time to initiate roots.*—About 14 days at temperatures of 21° C.

*Time to develop roots.*—About 30 days at temperatures of 21° C.

*Rooting habit.*—Young plants, vigorous and fibrous; older plants becoming woody.

Plant description:

*Plant form and growth habit.*—Perennial, mounded foliage with numerous upright and strong flowering stems.

*Vigor.*—Vigorous, rapid growth rate.

*Crop time.*—From cuttings of rooted tissue-cultured plantlets, about nine months are required to produce mature flowering plants. Plants typically produced in 15-cm containers.

*Plant height, soil level to top of foliage.*—9 to 12 cm.

*Plant height, soil level to top of flowers.*—About 65 cm.

*Plant diameter.*—30 to 40 cm.

Foliage description:

*Arrangement.*—Rosette, single.

*Length.*—9 to 12 cm.

*Width.*—9 to 11 cm.

*Shape.*—Rounded cordate, 7-lobed.

*Apex.*—Broadly obtuse, lobed.

*Base.*—Cordate.

*Margin type.*—Crenate, ciliate.

*Venation pattern.*—Reticulate.

*Texture.*—Slightly rough, slight pubescence on both surfaces.

*Color.*—Marbled effect of dark green veins with silver green interveinal areas.

Young foliage, upper surface: 198A.

Young foliage, lower surface: 187A.

Mature foliage, upper surface: 198A.

Mature foliage, lower surface: 187A.

Venation, upper surface: 131A underlain with 200A.

Venation, lower surface: 187A.

*Petiole.*—Length: 11 to 14 cm.

Diameter: About 2 mm.

Color: 187B.

*Durability of foliage to stress.*—High.

Flower description:

*Natural flowering season.*—Spring through summer, May through August in the Northern Hemisphere.

*Flower arrangement.*—Numerous single flowers arranged on evenly feathery conical panicles on upper half of flowering stem; usually about 100 to 150 flowers per flowering stem. Flowering stems uniform in shape and dense with numerous flowers. Flowering continuous with numerous flowering stems forming throughout flowering period; usually about 16 to 18 flowering stems per plant. Flowering stems often produce lateral shoots at base.

*Flowering stem length.*—About 40 to 65 cm.

*Flower appearance.*—Campanulate, persistent. Individual flowers last about one week on plant.

*Fragrance.*—None detected.

*Flower diameter.*—About 4.5 cm.

*Flower depth (height).*—About 7 mm.

*Flower bud.*—Length: About 4 mm.

Diameter: About 2.5 mm.

Shape: Bulbous.

Color: 63C.

Rate of opening: About 2 to 3 days.

*Petals.*—Appearance: Thin.

Texture: Slightly pubescent.

Arrangement: Radially symmetrical with five petals.

Shape: Spatulate.

Apex: Acute.
Margin: Dentate.
Length: About 4 mm.
Width: About 1 mm.
Color:
When opening, inner surface: White.
When opening, outer surface: White.
Fully opened, inner surface: White.
Fully opened, outer surface: 62B.
*Sepals/calyx.*—Appearance: Five sepals fused into a radially symmetrical calyx tube.
Sepal apex: Obtuse.
Sepal margin: Entire.
Sepal texture: Thin, pubescent.
Sepal color: 63C.
Calyx length: About 6 mm.
Calyx diameter: About 4.5 mm.
*Peduncles.*—Angle: Erect.
Strength: Strong.
Color: 59B.
Length: About 2.5 mm.
Angle: Horizontal to drooping.
Strength: Strong.
Color: 59B.
*Reproductive organs.*—Androecium:
Stamen number: Five.
Anther shape: Oval.
Anther size: About 0.2 mm.
Anther color: 24A.
Amount of pollen: Moderate.
Pollen color: 8A.
Gynoecium:
Pistil number: Two.
Pistil length: About 6 mm.
Stigma shape: Rounded.
Stigma color: 157C.
Style length: About 4 mm.
Style color: 157C.
Ovary color: 157C.
*Seed description.*—Length: About 0.6 mm.
Diameter: About 0.3 mm.
Color: Black.
Disease Resistance: Under commercial conditions, no resistance to diseases common to Heuchera have been observed.

It is claimed:

1. A new and distinct Heuchera plant named 'Harmonic Convergence', as illustrated and described.

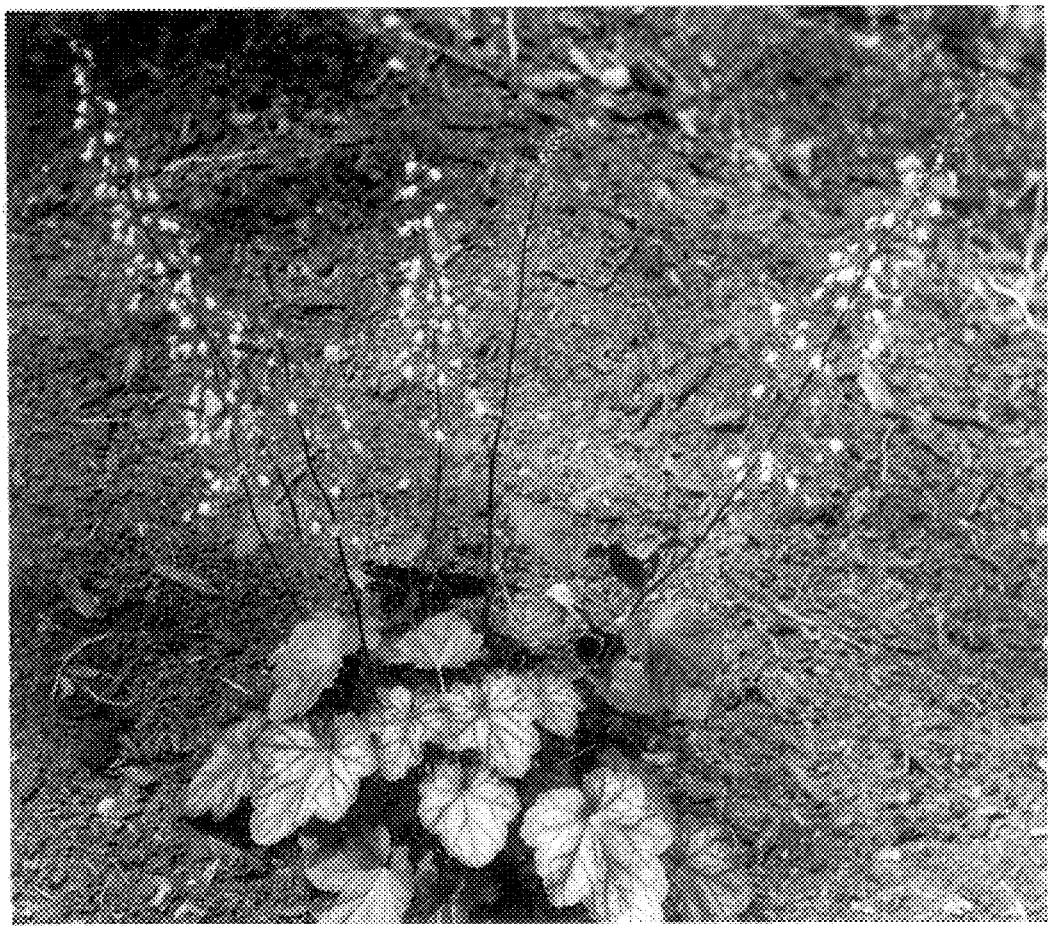
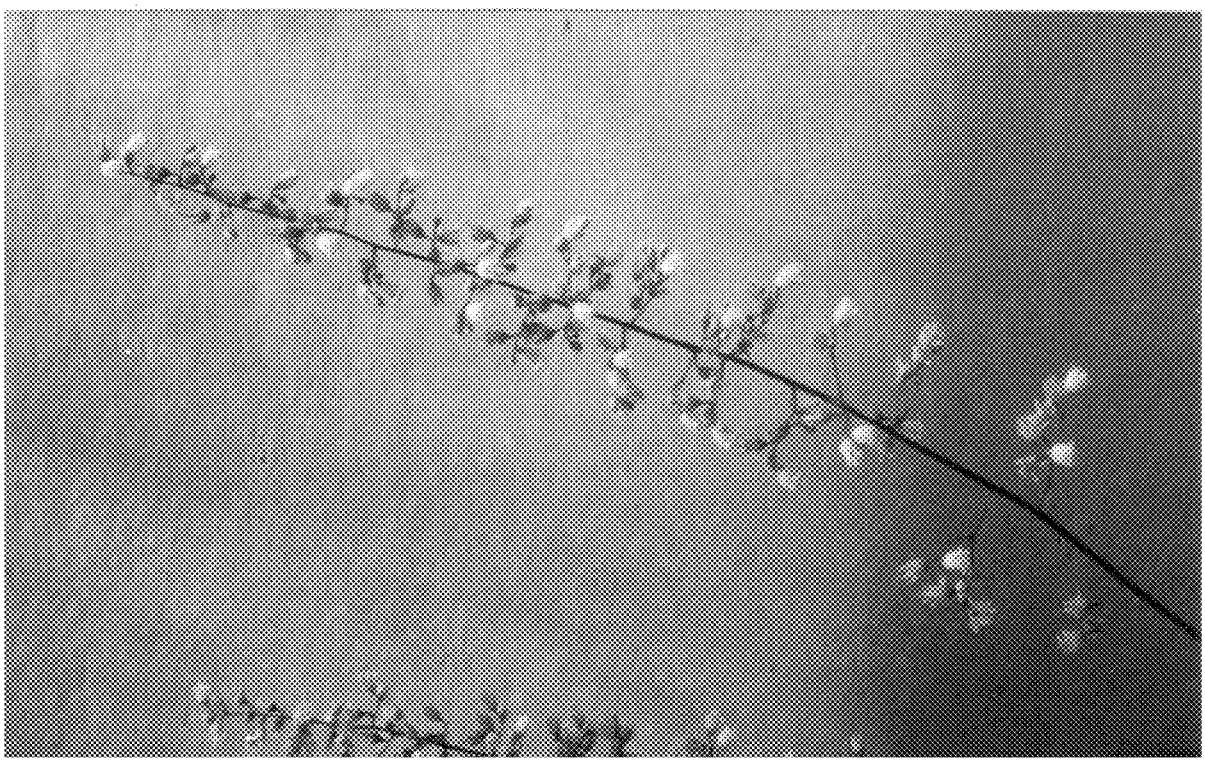

* * * * *